United States Patent [19]

Weers et al.

[11] Patent Number: 5,047,069

[45] Date of Patent: Sep. 10, 1991

[54] ANTIOXIDANTS FOR LIQUID HYDROCARBONS

[75] Inventors: Jerry J. Weers, Ballwin; Thomas V. Bagwell, St. Louis, both of Mo.

[73] Assignee: Petrolite Corporation, St. Louis, Mo.

[21] Appl. No.: 601,151

[22] Filed: Oct. 22, 1990

Related U.S. Application Data

[63] Continuation of Ser. No. 386,337, Jul. 27, 1989, abandoned.

[51] Int. Cl.$^5$ ................................................ C10L 5/00
[52] U.S. Cl. ........................................ 44/334; 44/415; 44/425; 544/145; 544/159; 544/173
[58] Field of Search ................... 44/415, 425, 334; 544/145, 159, 173

[56] References Cited

U.S. PATENT DOCUMENTS

| | | | |
|---|---|---|---|
| 2,684,293 | 7/1954 | Hill | 44/73 |
| 3,269,810 | 8/1966 | Chamot | 44/73 |
| 3,649,229 | 3/1972 | Otto | 44/73 |
| 3,877,889 | 4/1975 | Dix | 44/73 |
| 3,920,415 | 11/1975 | Reusser et al. | 44/75 |
| 4,006,089 | 2/1977 | Chibnik | 44/73 |
| 4,166,726 | 9/1979 | Harle | 44/73 |
| 4,501,595 | 2/1985 | Sung et al. | 44/74 |
| 4,553,979 | 11/1985 | Hanlon et al. | 44/73 |

Primary Examiner—Margaret B. Medley
Attorney, Agent, or Firm—Jeffrey S. Boone; Kenneth Solomon

[57] ABSTRACT

An antioxidant for liquid hydrocarbons such as fuels has the structure

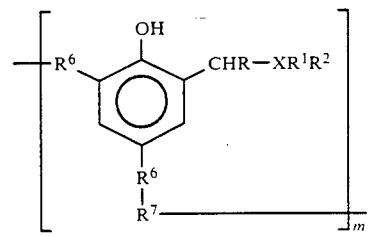

wherein X is N or S; R is H or a $C_1$ to $C_5$ alkyl moiety; $R^1$ and $R^2$ are each independently $C_5$ to $C_{18}$ alkyl or cycloalkyl moieties (which may optionally contain a hetero atom such as oxygen), only one of $R^1$ and $R^2$ being present if X is S, or may be combined to form a 5 or preferably 6 membered ring; each $R^6$ is independently the residue of a $C_1$ to $C_5$ aldehyde; and $R^7$ is the residue of a polyamine of the formula

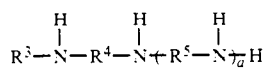

wherein $R^3$ is a $C_8$ to $C_{50}$ alkyl moiety (which may optionally contain one or more ether linkages); $R^4$ and $R^5$ are each independently $C_2$ to $C_6$ alkylene moieties; a is 0 or 1; and m is at least 3.

23 Claims, No Drawings

ANTIOXIDANTS FOR LIQUID HYDROCARBONS

This application is a continuation of application Ser. No. 07/386,337, filed July 27, 1989 now abandoned.

BACKGROUND OF THE INVENTION

This invention concerns antioxidants for liquid hydrocarbons, such as petroleum distillates, including fuels. More particularly, this invention relates to such antioxidants which are condensation polymers of certain amino- or thio-alkylene-substituted phenols, lower aliphatic aldehydes, and certain alkylene polyamines.

The catalytic cracking of petroleum to form fuels is a well established method of manufacture. Cracking is the process of converting large hydrocarbon molecules into smaller ones by the application of heat and/or catalysts. However, the products formed by cracking have an undesirable tendency to develop unstable products in many fractions, particularly in the mid-distillate fuels. Under storage and use conditions these products form sludges or gums and also tend to discolor the fuels. The presence of minute quantities of metals such as iron and copper accelerate the degradation process—acting as catalysts in the degradation of hydrocarbons. In order to retard the formation of sludges or gums by degradation, many additives have been proposed which function as stabilizers or antioxidants for the fuel fractions. Other additives are employed as metal deactivators—serving the function of retarding the catalytic effect of metals in the degradation process. One of the requisites for additives for fuels is that they must provide the stabilization, antioxidant properties or metal deactivating properties in very small concentrations in the fuel, so as not to interfere with the performance of the fuels in internal combustion engines.

U.S. Pat. No. 3,269,810 (Chamot Nalco, 1966) discloses a very broad class of structurally related antioxidants/chelants for use in gasolines. While the chelant activity of these materials is good, they are only marginally effective as antioxidants.

Co-pending application Ser. No. 383,941, filed July 21, 1989, titled Antifoulant Compositions and Methods, now U.S. Pat. No. 4,900,427 discloses structurally related refinery antifoulants. These materials also act as antioxidants, but cannot be used as such in sufficient concentration in fuels due to their tendency to cause emulsions when water is present.

Accordingly, it would be desirable to provide an antioxidant for liquid hydrocarbons such as fuels, which would have a high level of antioxidant activity, but not contribute to the formation of emulsions.

SUMMARY OF THE INVENTION

Briefly, the invention comprises a polymer which is the reaction product of certain amino- or thio-alkylene-substituted phenols, a $C_1$ to $C_5$ aldehyde, and a polyamine having a $C_8$ to $C_{50}$ terminal alkyl moiety. Such compounds have the general structure:

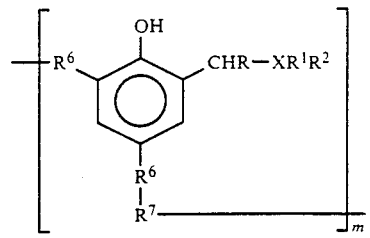

wherein X is N or S; R is H or a $C_1$ to $C_5$ alkyl moiety; $R^1$ and $R^2$ are each independently $C_5$ to $C_{18}$ alkyl or cycloalkyl moieties which may optionally contain a hetero atom, only one of $R^1$ and $R^2$ being present if X is S, or may be combined to form a 5 or preferably 6 membered ring; each $R^6$ is independently the residue of a $C_1$ to $C_5$ aldehyde; and $R^7$ is independently the residue of a $C_1$ to $C_5$ aldehyde; and $R^7$ is the residue of a polyamine of the formula

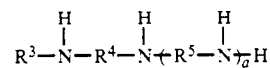

wherein $R^3$ is a $C_8$ to $C_{50}$ alkyl moiety which may optionally contain one or more ether linkages; $R^4$ and $R^5$ are each independently $C_2$ to $C_6$ alkylene moieties; a is 0 or 1; and m is at least 3.

The invention also comprises a liquid hydrocarbon containing the aforementioned polymer.

The polymers of the invention are useful in liquid hydrocarbons to prevent oxidation, discolorization, and residue formation. The compounds of the invention do not cause the emulsions associated with related compounds and do not cause destructive sequestering of metals (i.e., they do not attack the metal containers in which they may be stored).

DETAILED DESCRIPTION OF THE INVENTION

One component useful in the production of the antioxidants of the invention is a substituted phenol of the formula

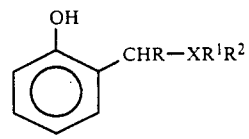

Wherein X is N or S; R is H or a $C_1$ to $C_5$ alkyl moiety, preferably H; $R^1$ and $R^2$ are each independently $C_5$ to $C_{18}$, preferably $C_6$ to $C_{12}$ alkyl or cycloalkyl moieties which may optionally contain a hetero atom, only one of $R^1$ and $R^2$ being present if X is S, or may be combined to form a 5 or preferably 6 membered ring. The substituted phenol is conveniently prepared by a conventional reaction of phenol, an aldehyde of the formula RHC=O, and an amine or thiol of the formula $R^1R^2XH$, wherein R, $R^1$, $R^2$, and X are defined as above. Preferred amines or thiols include cyclohexylamine (aminocyclohexane), morpholine (tetrahydro-1,4-oxazine), and n-dodecylmercaptan (1-dodecanethiol). The reaction is preferably carried out by mixing phenol and the amine or thiol in a solvent such as xylene, heating to about 60° C., dripping in the aldehyde in the form of an aqueous solution, allowing time for a complete reaction (about 1 hour), and distilling off the water.

The compounds of the invention are conveniently prepared by reacting the substituted phenol with an aldehyde of the formula $R^6HC=O$, wherein $R^6$ is H or a $C_1$ to $C_5$ alkyl moiety; and a polyamine of the formula

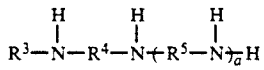

wherein $R^3$ is a $C_8$ to $C_{50}$, desirably $C_{12}$ to $C_{40}$, preferably $C_{14}$ to $C_{32}$, more preferably $C_{14}$ to $C_{22}$ alkyl moiety which may optionally contain one or more ether linkages; $R^4$ and $R^5$ are each independently $C_2$ to $C_6$, preferably $C_2$ to $C_4$, more preferably $C_2$ or $C_3$, and most preferably a $C_2$ alkylene moiety; and a is 0 or 1, preferably 1.

The choice of aldehyde has little influence on the reaction product, except that higher aldehydes are less reactive and produce lower yields. Formaldehyde is therefore preferred for reasons of cost, availability, and reaction yield. Formaldehyde may be used in its gaseous form or in other forms such as the solid paraformaldehyde or formaldehyde dissolved in an aqueous medium or in nonaqueous polar media such as isopropanol.

Formalin is an example of an aqueous formaldehyde solution of about 37% concentration. Special precautions usually are employed when the aldehyde reactant is an aqueous solution, such as formalin. For example, it is necessary to remove the water of the formalin solution during or after the condensation reaction—e.g., by application of vacuum to the reaction vessel or by dissolving the condensation product during the condensation reaction in a water immiscible solvent such as benzene, toluene, or xylene, and then separating the water and solvent. The condensation takes place in the presence of water, but it is necessary to separate water from the reactants during the condensation reaction if high degrees of condensation are to be achieved.

The aldehyde is preferably added at 2 to 2.7 moles per mole of substituted phenol. Larger amounts cause substantial unreacted aldehyde to be present in the reaction product and lower amounts cause lowered antioxidant activity in the product.

The polyamine is conveniently derived from natural sources and will therefor comprise a blend of chain lengths. An exemplary polyamine is N-tallow diethyltriamine.

The reaction is a Mannich base reaction which is described generally in *Synthesis* 703-775 (1973). General methods of preparation of the compositions of the invention are illustrated below:

(a) The polyamine is mixed with the substituted phenol and the mixture is cooled to 0°-10° C. The aqueous aldehyde solution is added dropwise while the reaction mixture is maintained at 0°-10° C. over a period of ½ to 2 hours. The reaction mixture is stirred for an additional hour. During this interval the reaction temperature is allowed to rise to room temperature, and the mixture is usually heated at 50°-60° C. for an additional hour. An aromatic solvent such as benzene, or preferably, xylene or toluene, is added to the mixture to dissolve the condensation product, and the water in the reaction mixture is separated from the organic solvent phase. The solution of the polymer may be used as such, or the solvent may be removed by vacuum distillation.

(b) The polyamine is mixed with the substituted phenol, and the mixture is cooled to room temperature. The aldehyde is added in small portions to the reaction mixture. The temperature is maintained at 25°-40° C. during the addition time of ½ to 2 hours. After all of the aldehyde has been added, the water is removed in the same manner as in (a).

(c) The polyamine is mixed with the substituted phenol, and the aqueous aldehyde solution is added in small portions over a period of ½ to 2 hours. During this period the temperature is allowed to rise to 50°-80° C. The reaction mixture is stirred at this temperature for an additional to 2 hours. The water is then removed by decanting from the condensation product, and the traces of Water in the condensation product are removed under vacuum at temperatures from 70°-150° C.

(d) The polyamine is mixed with the substituted phenol, and the aqueous aldehyde solution is added to the mixture in a short time interval. The reaction mixture is then heated at 60°-80° C. for ½ to 6 hours. The reaction mixture is cooled and the water is removed either by decanting, by vacuum distillation, or by separation after the product has been dissolved in an organic solvent.

(e) The polyamine is mixed with the substituted phenol, and solid paraformaldehyde is added in portions over a period of ½ to 2 hours. The reaction temperature is maintained at 50°-80° C. for a period of ½ to 2 hours after the paraformaldehyde has been added. The reaction mixture is cooled to room temperature and may be used as is.

(f) The polyamine is mixed with the substituted phenol, and formaldehyde in isopropanol solution is slowly added over a period of ½ to 2 hours. The reaction mixture is stirred for ½ to 2 hours. The product may be used in this way or the solvent may be removed under vacuum. The temperature during the reaction may rise to 50°-80° C.

(g) The reaction is performed as in (a), (b), or (c) above. The water is removed by vacuum distillation (10-20 mm) at temperatures not to exceed 100° C.

(h) The reaction is performed as in (a)-(f) above. The water is removed under vacuum and at temperatures of 100°-160° C.

A specific method is taught in the examples.

The compounds of the invention are believed to have the following structure:

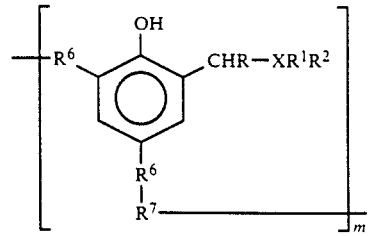

wherein X is N or S; R is H or a $C_1$ to $C_5$ alkyl moiety; $R^1$ and $R^2$ are each independently $C_5$ to $C_{18}$ alkyl or cycloalkyl moieties (which may optionally contain a hetero atom such as oxygen), only one of $R^1$ and $R^2$ being present when X is S, or may be combined to form a single $C_5$ to $C_{18}$ ring; each $R^6$ is independently the residue of a $C_1$ to $C_6$ aldehyde; and $R^7$ is the residue of a polyamine of the formula

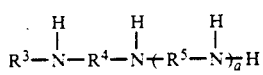

wherein $R^3$ is a $C_8$ to $C_{50}$ alkyl moiety; $R^4$ and $R^5$ are each independently $C_2$ to $C_6$ alkylene moieties; a is 0 or 1; and m is at least 3. The degree of polymerization is difficult to determine with conventional analytical equipment. However, it is known that suitable materials have at least 3 repeating units.

Because the products of the invention are typically made from natural products such as tallow derivatives, they often contain minor amounts of numerous isomers, homologs, and impurities. To prevent these minor components from forming a residue in the product solution, it is advantageous to add up to about 5% (based on the weight of the reaction product) of a solvent such as an alcohol, particularly 2-methylpentanol.

The products of the invention are useful as antioxidants for liquid hydrocarbons, particularly fuels, and more particularly fuels such as kerosene, diesel fuel, and gasoline. Kerosene and diesel fuel are exemplary fuels. In such applications the compounds of the invention prevent discoloration and residue formation, and also sequester metals which can cause degradation.

The compounds of the invention are effective in minor amounts; for example, 0.5 to 500, preferably 5 to 400, and more preferably 10 to 300 ppm (parts per million) in the liquid hydrocarbon. The compounds may simply be blended into the hydrocarbon by any convenient means. No special equipment or procedure is necessary.

The invention will be further illustrated by the following examples. In the examples, all parts and percentages are by weight unless otherwise specified.

EXAMPLE 1

10.4 g of 90% (aqueous) phenol was put in a 3 necked flask and 60 g of xylene bottoms (as solvent) added. The mixture was stirred while 8.7 g of morpholine (tetrahydro-1,4-oxazine) was added. An exothermic reaction occurred which raised the temperature of the mixture 5°-10° C. above room temperature. The mixture was then heated to 80°-85° C. and 8.1 g of 37% aqueous formaldehyde was added dropwise over 15 minutes. Stirring and heating was continued for another 45 minutes, followed by the addition of 43 g of N-tallow diethyltriamine (sold as Armak Triamine T by Akzo) in a single portion. Continuing to heat to 80°-85° C., the mixture was stirred for 15 minutes and 21.9 g of 37% formaldehyde was then added dropwise over 20 minutes. Heating was continued for 1 hour and the mixture was then transferred to a separating funnel. 24.2 g of aqueous phase was removed and the organic phase returned to the reaction flask. 2.3 g of residual water was distilled off and distillation continued until the temperature reached 150° C. The mixture was then cooled, leaving 122 g of product which was an amber oil.

EXAMPLE 2

In a manner similar to Example 1, a compound was made using cyclohexylamine instead of morpholine, and N-isodecyloxypropyl-1,3-diaminopropane sold as Tomah DA-14 by Exxon instead of N-tallow diethyltriamine.

EXAMPLE 3

In a manner similar to Example 2, a compound was made, substituting N-ethylcyclohexylamine for the cyclohexylamine.

EXAMPLE 4

The products of Examples 1-3 were added to a #2 diesel oil containing a caustic-washed coker distillate. The fuel was aged at 110° F. (43° C.) (ASTM D4625-86) and evaluated for color (ASTM D1500-87) and light transmittance at 540 nm at 4 weeks and 8 weeks. The results are reported in Table I.

TABLE I

| | Initial Color: <2.5 | | | | |
| | Initial Transmittance: 61% | | | | |
| | Concentration[1] | 4 weeks | | 8 weeks | |
| Additive | (ppm) | color[2] | trans(%)[3] | color | trans(%) |
|---|---|---|---|---|---|
| None* | 0 | <3.5 | 31 | <4.5 | 12 |
| Example 1 | 50 | <3.0 | 44 | <4.0 | 18 |
| " | 200 | <3.0 | 47 | <3.5 | 27 |
| Example 2 | 50 | <3.0 | 40 | <4.0 | 17 |
| " | 200 | <3.0 | 47 | <3.5 | 27 |
| Example 3 | 50 | 3.0 | 38 | 4.0 | 15 |
| " | 200 | <3.0 | 42 | <4.0 | 20 |

*Not an example of the invention.
1. Based on active ingredient, ignoring any solvent present.
2. Lower values are better.
3. Higher values are better.

EXAMPLE 5

The products of Examples 1-2 were added to a light cycle oil and heated to 300° F. (149° C.) for 3 hours. The color, transmittance, and filterable solids ("pad" rating, DuPont Blotter Test F-21 ["300° stress test]), were then measured. The data are reported in Table II.

TABLE II

| | Initial Color: 1.5 | | | |
| | Initial Transmittance: 71% | | | |
| Additive | Concentration (ppm) | color | trans(%) | pad[4] rating |
|---|---|---|---|---|
| None* | 0 | <4.0 | 17 | 2 |
| Example 1 | 50 | <3.0 | 39 | 2 |
| Example 2 | 50 | 3.0 | 32 | 2 |

*Not an example of the invention.
4. Lower values are better.

EXAMPLE 6

Following the procedure of Example 1, except that a larger amount of formaldehyde was added to the final reaction step (3.7 molar equivalents, based on the substituted phenol), a similar compound was made.

EXAMPLE 7

The compound of Example 1 and the compound of Example 6 were added to a #2 diesel oil and heated to 300° F. (149° C.) for 90 minutes. The color, transmittance, and pad rating were then measured. The results are shown in Table III.

TABLE III

| Additive | Concentration (ppm) | color | trans(%) | pad rating |
|---|---|---|---|---|
| None* | 0 | 5.0 | 7 | 14 |
| Example 1 | 15 | 5.0 | 6 | 14 |
| " | 30 | 3.0 | 29 | 9 |
| " | 60 | 2.5 | 41 | 5 |
| Example 6 | 15 | <2.5 | 46 | 4 |
| " | 30 | <2.5 | 42 | 4 |
| " | 60 | <2.5 | 46 | 4 |

Initial Color: <2.0
Initial Transmittance: 76%

*Not an example of the invention.

EXAMPLE 8

Following the procedure of Example 8, the compounds of Examples 1 and 6 were added to a cracked gas oil and evaluated. The results are shown in Table IV.

TABLE IV

| Additive | Concentration (ppm) | color | trans(%) | pad rating |
|---|---|---|---|---|
| None* | 0 | 2.5 | 32 | 2 |
| Example 1 | 50 | 2.5 | 36 | 2 |
| " | 100 | 2.0 | 42 | 2 |
| " | 300 | 2.0 | 46 | 2 |
| Example 6 | 50 | 2.5 | 42 | 2 |
| " | 100 | <2.5 | 43 | 2 |
| " | 300 | 2.0 | 49 | 2 |

Initial Color: <2.0
Initial Transmittance: 55%

*Not an example of the invention.

EXAMPLE 9

Following the procedures of Example 8, the compounds of Examples 1 and 6 were added to another #2 diesel oil and evaluated. The results are shown in Table V.

TABLE V

| Additive | Concentration (ppm) | color | trans(%) | pad rating |
|---|---|---|---|---|
| None* | 0 | 4.5 | 7 | 1 |
| Example 1 | 15 | <4.0 | 14 | 1 |
| " | 30 | 3.5 | 18 | 1 |
| " | 60 | 3.5 | 23 | 1 |
| Example 6 | 15 | <4.0 | 13 | 1 |
| " | 30 | 3.5 | 18 | 1 |
| " | 60 | 3.5 | 21 | 1 |

Initial Color: <1.5
Initial Transmittance: 81%

*Not an example of the invention.

EXAMPLE 10

The compound of Example 6 was added to a blend of 80% straight run distillate and 20% light cycle oil, and the mixture was then heated at 110° F. (43° C.) for 12 weeks. The mixture was then evaluated for color, light transmittance, and residue (ASTM D4625-86). The results are reported in Table VI.

TABLE VI

| Additive | Concentration (ppm) | color | trans(%) | Residue (mg/100 mL) |
|---|---|---|---|---|
| None* | 0 | <4.0 | 15 | 2.9 |
| Example 6 | 15 | 3.5 | 20 | 2.1 |

Initial Color: <1.0
Initial Transmittance: 88%

*Not an example of the invention.

EXAMPLE 11

In a manner similar to Example 10, the compound of Example 6 was added to a #2 diesel oil and heated to 300° F. (149° C.) for 90 minutes. The mixture was then evaluated and the results are reported in Table VII.

TABLE VII

| Additive | Concentration (ppm) | color | trans(%) | pad rating |
|---|---|---|---|---|
| None* | 0 | 5.5 | 3 | 17 |
| Example 6 | 15 | <3.0 | 32 | 4 |

Initial Color: <2.0
Initial Transmittance: 76%

*Not an example of the invention.

What is claimed is:

1. The polymeric reaction product of
(a) an ortho-substituted phenol of the formula

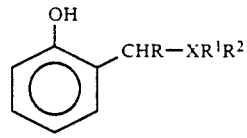

(b) a polyamine of the formula

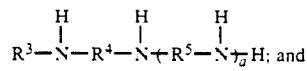

(c) a $C_1$ to $C_6$ aldehyde;
wherein X is N or S; R is H or a $C_1$ to $C_5$ alkyl moiety; $R^1$ and $R^2$ are each independently $C_5$ to $C_{18}$ alkyl or cycloalkyl moieties which may optionally contain a hetero atom, only one of $R^1$ and $R^2$ being present if X is S, or may be combined to form a 5 or 6 membered ring; $R^3$ is a $C_8$ to $C_{50}$ alkyl moiety which may optionally contain one or more ether linkages; $R^4$ and $R^5$ are each independently $C_2$ to $C_6$ alkylene moieties; and a is 0 or 1.

2. The product of claim 1 wherein R is H and said $C_1$ to $C_5$ aldehyde is formaldehyde.

3. The product of claim 1 wherein X is N.

4. The product of claim 3 wherein $R^1$ and $R^2$ are combined to form a ring.

5. The product of claim 4 wherein the ring has 6 members.

6. The product of claim 5 wherein one of the members of the ring is oxygen.

7. The product of claim 1 wherein a is 1.

8. The product of claim 1 wherein $R^4$ and $R^5$ each independently have 2 or 3 carbon atoms.

9. The product of claim 1 wherein $R^3$ contains an ether linkage.

10. A compound of the formula

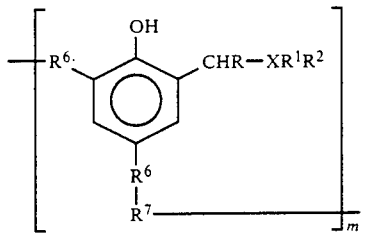

wherein X is N or S; R is H or a $C_1$ to $C_5$ alkyl moiety; $R^1$ and $R^2$ are independently $C_5$ to $C_{18}$ alkyl or cycloalkyl moieties which may optionally contain a hetero atom, only one of $R^1$ and $R^2$ being present if X is S, or may be combined to form a 5 or 6 membered ring; each $R^6$ is independently the residue of a $C_1$ to $C_5$ aldehyde; and $R^7$ is the residue of a polyamine of the formula

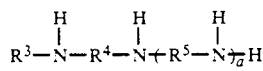

wherein $R^3$ is a $C_8$ to $C_{50}$ alkyl moiety which may optionally contain one or more ether linkages; $R^4$ and $R^5$ are each independently $C_2$ to $C_6$ alkylene moieties; a is 0 or 1; and m is at least 3.

11. The compound of claim 10 wherein each $R^6$ is the residue of formaldehyde.

12. The compound of claim 10 wherein X is N.

13. The compound of claim 12 wherein $R^1$ and $R^2$ are combined to form a ring.

14. The compound of claim 13 wherein the ring has 6 members.

15. The compound of claim 14 wherein one of the members of the ring is oxygen.

16. The compound of claim 10 wherein a is 1.

17. The compound of claim 10 wherein $R^4$ and $R^5$ each independently have 2 or 3 carbon atoms.

18. The compound of claim 10 wherein $R^3$ contains an ether linkage.

19. A liquid hydrocarbon containing the product of claim 1 in an amount sufficient to inhibit oxidation.

20. The liquid hydrocarbon of claim 19 wherein the liquid hydrocarbon is fuel.

21. The liquid hydrocarbon of claim 20 wherein the fuel is kerosene, diesel fuel, or gasoline.

22. The liquid hydrocarbon of claim 21 wherein the fuel is kerosine or diesel fuel.

23. The liquid hydrocarbon of claim 19 wherein the product of claim 1 is present at 0.5 to 500 ppm.

* * * * *